(12) United States Patent
Wosikowski-Buters et al.

(10) Patent No.: US 7,659,396 B2
(45) Date of Patent: Feb. 9, 2010

(54) METHOD FOR THE PRODUCTION OF PHENYLALANINE DERIVATIVES

(75) Inventors: Katja Wosikowski-Buters, Poing (DE); Stefan Sperl, Munich (DE); Joachim Sommer, Wolfersheim (DE)

(73) Assignee: Wilex AG, Muchen (DE)

( * ) Notice: Subject to any disclaimer, the term of this patent is extended or adjusted under 35 U.S.C. 154(b) by 273 days.

(21) Appl. No.: 11/749,579

(22) Filed: May 16, 2007

(65) Prior Publication Data

US 2009/0005562 A1 Jan. 1, 2009

Related U.S. Application Data

(62) Division of application No. 10/522,218, filed on Jan. 24, 2005, now Pat. No. 7,247,724.

(51) Int. Cl.
*C07D 241/04* (2006.01)
*C07C 229/00* (2006.01)
*C07C 205/00* (2006.01)

(52) U.S. Cl. .................. 544/388; 560/40; 562/435

(58) Field of Classification Search .............. 544/388; 560/40; 562/435
See application file for complete search history.

(56) References Cited

U.S. PATENT DOCUMENTS 6,624,169 B1  9/2003  Wilhelm et al.

FOREIGN PATENT DOCUMENTS

WO   WO 92/08709 A   5/1992

OTHER PUBLICATIONS

Lee K et al, "Fluorobenzamidrazone Thrombin Inhibitors: Influence of Fluorine on Enhancing Oral Absorption" Bioorganic & Medicinal Chemistry Letters, Oxford GB, Bd 9, Nr. 17, Sep. 6, 1999, Seiten 2483-2486, XP004188848 ISSN: 0960-.
PCT International Preliminary Examination Report, Oct. 7, 2004, IPEA/EP.

*Primary Examiner*—Jafar Parsa
(74) *Attorney, Agent, or Firm*—Cook Alex Ltd.

(57) ABSTRACT

The invention relates to an improved method for the production of 3-amidino- or 3-guanidinophenylalanine derivatives, especially triisopropylphenyl-sulfonyl-substituted 3-amidino- or 3-guanidinophenylalanine derivatives.

4 Claims, 4 Drawing Sheets

METHOD FOR THE PRODUCTION OF PHENYLALANINE DERIVATIVES

Figure 1:
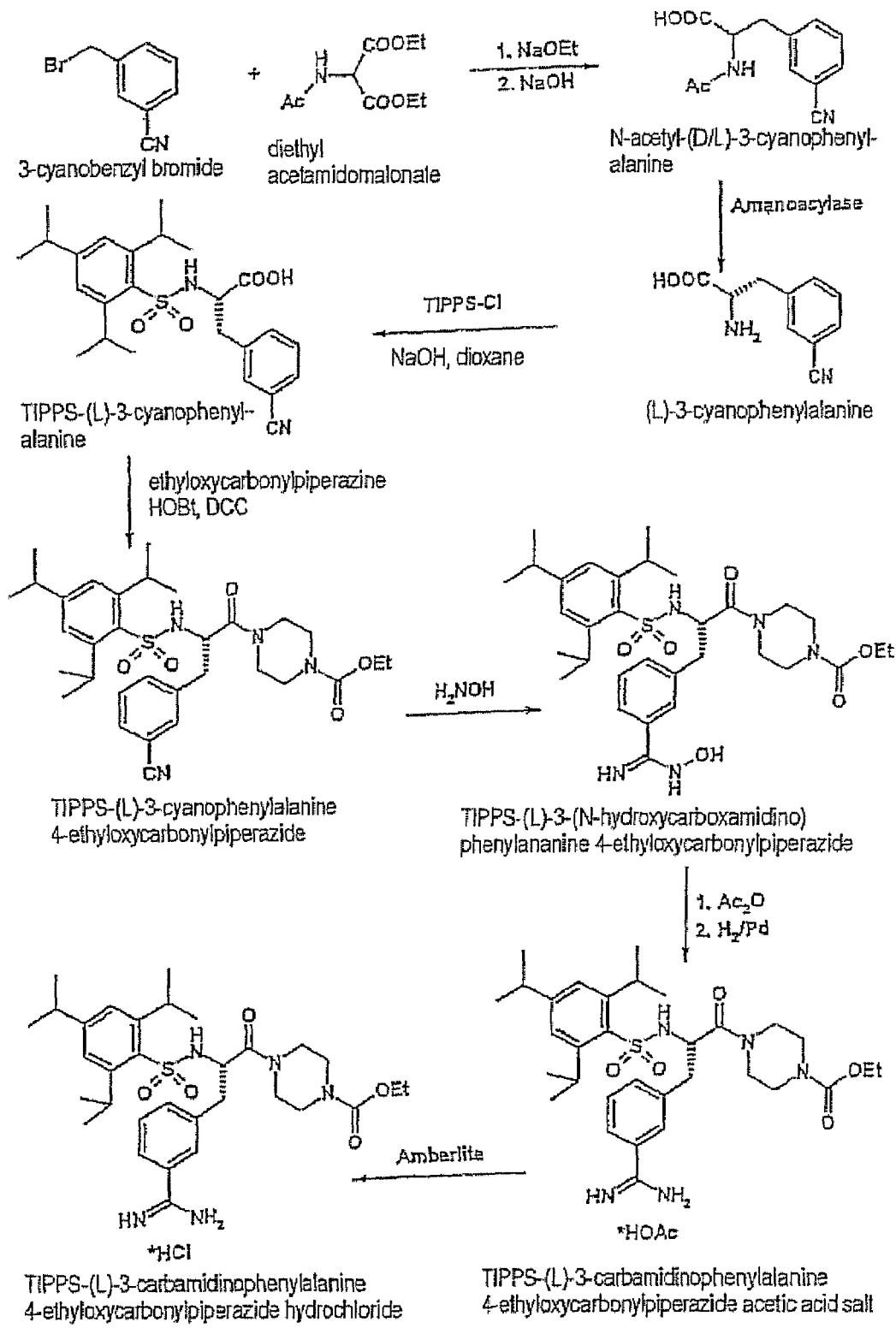

The present application claims priority to and a division of U.S. patent application Ser. No. 10/522,218 filed on Jan. 24, 2005 and now U.S. Pat. No. 7,247,724 which is incorporated herein by reference.

The invention relates to an improved method for the production of 3-amidino- or 3-guanidinophenylalanine derivatives, in particular of triisopropylphenyl-sulfonyl-substituted 3-amidino- or 3-guanidinophenylalanine derivatives.

The preparation of 3-amidinophenylalanine derivatives, in particular of Nα-(2,4,6-triisopropylphenylsulfonyl)-3-amidino-(L)-phenylalanine 4-ethoxycarbonylpiperazide (WX-UK1) and the use thereof as urokinase inhibitors is described for example in CH-A-6 89 611, WO 00/04954 and WO 00/17158 and in the publication of Stürzebecher et al. (Bioorg. Med. Chem. Let. 9 (1999), 3147-3152). DE 102 25 876.7 describes the preparation of guanidinophenylalanine derivatives as urokinase inhibitors. The synthetic methods used therein are straightforwardly reproducible on the laboratory scale, but are too elaborate and too costly for industrial applications. A particular problem is the synthesis of the precursor 2,4,6-triisopropylphenylsulfonyl (TIPPS)-(L)-3-cyanophenylalanine by reacting (L)-3-cyanophenyl-alanine and TIPPS-Cl. This reaction generally affords relatively low yields of product not exceeding 45%, because 53% of hydrolyzed TIPPS-OH result as unwanted byproduct. In addition, the desired reaction product can be separated from the byproduct only by elaborate chromatographic methods A further problem is that no cost-effective method for preparing the 3-cyanophenyl-alanine used as starting material was known.

The object of the present invention was to overcome at least in part the disadvantages of the synthetic method known in the art.

This object is achieved by a method for the production of 3-amidino- or 3-guanidinophenylalanine derivatives, comprising one or more of the following measures:

(a) use of 3-cyanobenzyl bromide as starting material, which is reacted with an N-protected aminomalonic diestez to give an N-protected cyanophenylalanine;

(b) workup of the product from the reaction of 3-cyanophenylalanine and an optionally substituted phenylsulfonyl halide, in particular 2,4,6-triisopropylphenylsulfonyl (TIPPS) halide, in an aqueous medium;

(c) reaction of an N-protected 3-cyanophenylalanine with a piperazine derivative to form an N-protected 3-cyanophenylalanine piperazide and subsequent reaction thereof with an optionally substituted phenylsulfonyl halide, in particular a TIPPS halide;

(d) reaction of 3-cyanophenylalanine with a quaternary ammonium hydroxide compound to give a 3-cyanophenylalanine ammonium salt and subsequent reaction thereof with an optionally substituted phenylsulfonyl halide, in particular a TIPPS halide;

(e) reaction of 3-cyanophenylalanine with a trialkylsilane compound to give a 3-cyanophenylalanine trialkylsilyl ester and subsequent reaction thereof with an optionally substituted phenylsulfonyl halide.

The present invention relates in particular to novel urokinase inhibitors derived from 3-amidino- or 3-guanidinophenylalanine of the general formula I

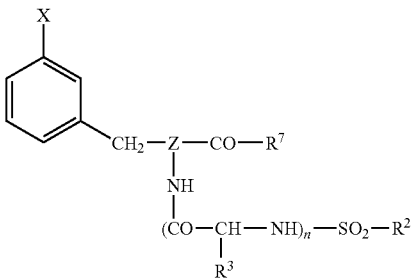

which are in the form of racemates and of compounds having the L or D configuration, and in which
X is an amidino or guanidino group,
$R^1$ is a group of the formula

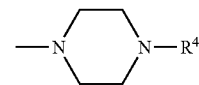

in which $R^4$ is
(i) an optionally substituted, e.g. by $C_1$-$C_6$-alkyl, $C_1$-$C_3$-alkoxy, hydroxyl, carboxyl, sulfonyl, nitro, cyano, oxo or/and halogen, $C_1$-$C_6$-alkyl radical such as, for example, ethoxycarbonyl, or aryl radical such as, for example, phenyl, p-halophenyl, naphthyl,
(ii) a saturated or unsaturated, branched or unbranched $C_1$-$C_6$-alkoxy radical or
(iii) an optionally substituted, e.g. by $C_1$-$C_6$-alkyl, $C_1$-$C_3$-alkoxy, hydroxyl, carboxyl, sulfonyl, nitro, cyano, oxo or/and halogen, phenoxy- or benzyloxycarbonyl radical,
$R^2$ is an optionally substituted, e.g. by $C_1$-$C_6$-alkyl, $C_1$-$C_3$-alkoxy, hydroxyl, carboxyl, sulfonyl, nitro, cyano, oxo or/and halogen, phenyl radical such as, for example, phenyl, 4-methylphenyl, 2,4,6-trimethylphenyl, 2,4,6-triisopropylphenyl, 4-methoxy-2,3,6-trimethylphenyl,
$R^3$ is H or branched or unbranched $C_1$-$C_4$-alkyl, and n is 0 or 1,
z is N or $CR^9$, where $R^9$ is H or branched or unbranched $C_1$-$C_4$-alkyl, and to the production thereof.

The compounds may also be in the form of salts, preferably of physiologically tolerated acid salts, e.g. of salts of mineral acids, particularly preferably of hydrochlorides, or of salts of suitable organic acids.

Particularly important compounds of those defined in the general claims are those in which $R^2$ is a mono-, di- or trialkyl-substituted phenyl radical, in particular a 2,4,6-substituted phenyl radical, e.g. a 2,4,6-triisopropylphenyl radical, and n is 0. Preference is further given to compounds in which Z is CH.

The compound of the formula (I) is particularly preferably Nα-(2,4,6-triisopropylphenylsulfonyl)-3-amidino-(D,L)-phenylalanine 4-ethoxycarbonylpiperazide, Nα-(2,4,6-triisopropylphenylsulfonyl)-3-guanidino-(D,L)-phenylalanine 4-ethoxycarbonylpiperazide, the L enantiomers thereof or pharmaceutically acceptable salts of these compounds.

In measure (a) there is preferably use of an N-acyl-protected aminomalonic diester, in particular an N-acetyl-protected aminomalonic diester such as, for example, diethyl acetamidomalonate. The use of the acetyl-valued diester is preferred because the corresponding acetylphenylalanine can be converted in the further synthesis into isomerically pure intermediates. The starting materials 3-cyanobenzyl bromide and the N-protected aminomalonic diester are commercially available and can be reacted in high yield to give an N-protected 3-cyanoophenylalanine.

According to measure (b) the product of the reaction of 3-cyanophenylalanine, in particular of (L)-3-cyanophenylalanine, and of an optionally mono- or polysubstituted, e.g. a sterically hindered phenylsulfonyl halide, in particular TIPPS-Cl, is worked up in an aqueous medium, preferably in water. The desired product is obtained in 95% or higher purity without chromatographic separation. Surprisingly, substantially qualitative removal of the unwanted phenylsulfonyl hydroxide, in particular TIPPS-OH, is possible in a simple manner.

Suitable substituents on the phenylsulfonyl halide are, for example, one or more $C_1$-$C_6$-, in particular $C_1$-$C_3$-alkyl radicals which may in turn be substituted one or more times, e.g. by halogen (e.g. trichloromethyl, trifluoromethyl), $C_1$-$C_6$-alkoxy radicals or/and halogens. Particular preference is given to triisopropylphenylsulfonyl chloride and to 4-methylphenylsulfonyl halides, 4-methoxyphenylsulfonyl halides, 4-methoxy-2,3,6-trimethylphenylsulfonyl halides, 2,2-dimethyl-6-methoxyphenylsulfonyl halides, trimethylphenylsulfonyl halides, trichloromethylphenylsulfonyl halides and trifluoromethylphenylsulfonyl halides.

According to measure (c), 3-cyanophenylalanine, in particular (L)-3-cyanophenylalanine, is converted into an N-protected derivative, e.g. a tBOC-protected derivative. This is followed by reaction with a piperazine derivative, e.g. ethoxycarbonylpiperazide to form an N-protected 3-cyanophenylalanine piperazide. This product is, after elimination of the protective group, subsequently reacted with an optionally substituted, e.g. a sterically hindered phenylsulfonyl halide, especially TIPPS-Cl. This reaction does not proceed with formation of the byproduct TIPPS-OH and therefore requires no additional steps to purify the desired product.

According to measure (d), 3-cyanophenylalanine, in particular (L)-3-cyanophenylalanine, is reacted with a quaternary ammonium hydroxide compound such as, for example, benzyltrimethylammonium hydroxide (Triton B) to give a 3-cyanophenylalanine ammonium salt. The product is subsequently reacted with an optionally substituted, e.g. a sterically hindered phenylsulfonyl halide, in particular TIPPS-Cl, with negligible formation of the byproduct TIPPS-OH, to give the desired product TIPPS-3-cyanophenylalanine. Preferred phenylsulfonyl halides are those indicated above under measure (b).

According to measure (e), 3-cyanophenylalanine, in particular (L)-3-cyanophenylalanine, is reacted firstly with a trialkylsilane compound. The compounds preferably employed as trialkylsilane compound are those in which the alkyl radicals are identical or different and each have 1 to 20, preferably 1 to 4, carbon atoms. Trimethylsilane is particularly preferably used. The reaction advantageously takes place in an anhydrous solvent, for example in dichloromethane. The free amino acid 3-cyano-phenylalanine is preferably suspended with an excess of trialkylsilane compound, for example 2 to 4, in particular 2.5 to 3 equivalents thereof in the solvent, for example in dichloromethane. There is intermediate formation thereby of the water-sensitive trialkylsilyl ester, for example the trimethylsilyl ester, as protection from dimerization and, through the simultaneous silylation of the amino group, the nucleophilicity is increased, thus speeding up the subsequent reaction with an optionally substituted phenylsulfonyl halide. Preferred phenylsulfonyl halides are those indicated above under measure (3)b. The 3-cyanophenylalanine trialkylsilyl ester formed as intermediate is then reacted with an optionally substituted phenylsulfonyl halide, in particular with triisopropylphenylsulfonyl chloride (TIPPS-Cl) to give the desired product TIPPS-3-cyanophenylalanine. It is advantageous to add a base, for example diisopropylethylamine (DIPEA), in this reaction. The desired product can be obtained in high yield and in high purity in this reaction.

The invention is further to be illustrated by the following figures and examples:

FIG. 1 shows a first embodiment of the method of the invention, comprising the use of measure (a), i.e. use of 3-cyanobenzylbromide and diethyl acetamidomalonate as starting materials. The reaction mixture on reaction of (L)-3-cyanophenylalanine and TIPPS-Cl can be worked up in aqueous medium (measure (b)).

Figure 2:
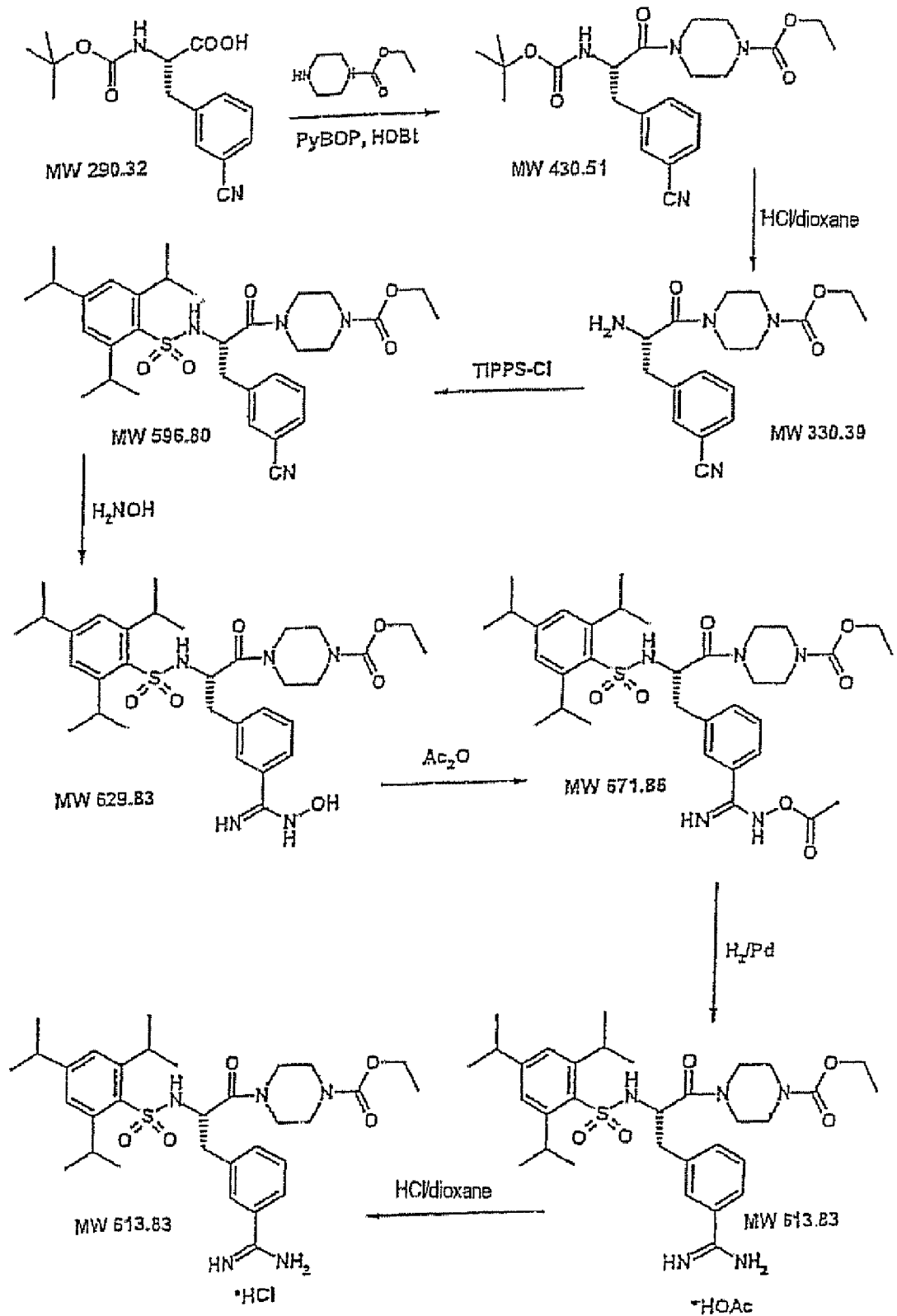

FIG. 2 shows a further embodiment of the method of the invention according to measure (c). A solution of (L)-3-cyanophenylalanine is reacted under Schotten-Baumann conditions with di-tert-butyl pyrocarbonate ($BOC_2O$) in order to obtain the corresponding BOC-protected amino acid (BOC-L-Phe(3-CN)—OH. The latter is reacted with N-ethoxycarbonylpiperazine and a suitable coupling reagent (for example DCC, HBTU, PyBOP or other reagents customarily employed in peptide chemistry) to give the corresponding amide BOC-L-Phe(3-CN)-Pip-COOEt. The BOC protective group is eliminated from the molecule by dissolving the compound in strong acids, (e.g. trifluoroacetic acid, HCl gas in dioxane or methanol). The free amino group produced thereby can be converted with addition of organic bases (e.g. triethylamine or diisopropylethylamine) in an anhydrous solvent with triisopropylphenylsulfonyl chloride (TIPPS-Cl) into the corresponding sulfonamide TIPPS-L-Phe(3-CN)-Pip-COOEt. The advantage of this reaction sequence is that the reaction with TIPPS-Cl can be carried out under anhydrous conditions, and thus no hydrolysis of the sulfonyl chloride to the sulfonic acid occurs. Preceding reaction of the free carboxylic acid function of BOC-L-Phe(3-CN)—OH with the piperazine also means that no side reactions occur, such as polymerization of the amino acid due to activation of the carboxylic acid by the sulfonyl chloride. The result is an enormous simplification of the workup of the compounds, justifying the two additional reaction steps required (reaction with $BOC_2O$ and later elimination of the BOC protective group by acid).

Figure 3:
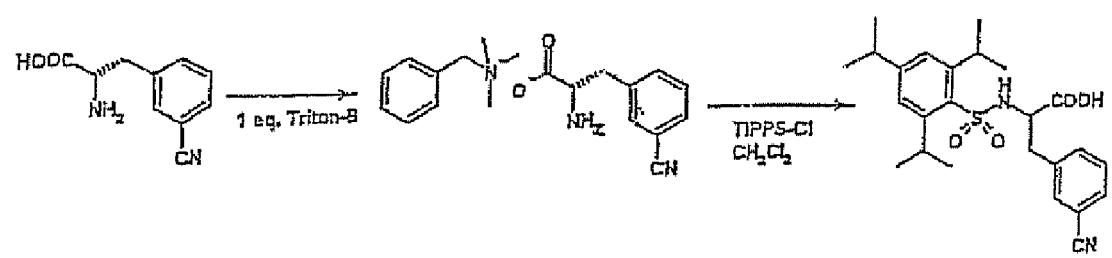

FIG. 3 shows a further embodiment of the method of the invention according to measure (d). The free amino acid L-3CN-Phe is dissolved together with one equivalent of an ammonium hydroxide compound, e.g. benzyltrimethylammonium hydroxide, in methanol, and the solvent is subsequently stripped off in vacuo. The water which is produced is removed by subsequent evaporation with toluene, because water forms an azeotrope with toluene. The resulting colorless oil is subsequently soluble in dichloromethane. In this or another suitable solvent, the reaction with TIPPS-Cl (slow addition while cooling) with addition of a tertiary amine, e.g. diisopropylethylamine, proceeds quantitatively with negligible side reactions within a few hours. After the solvent has been stripped off, the crude product is dissolved in ethyl acetate and subjected to acidic and neutral washes, the organic phase is dried, and the solvent is stripped off in vacuo. The product is converted into a foam from ether in vacuo and dried.

Figure 4:
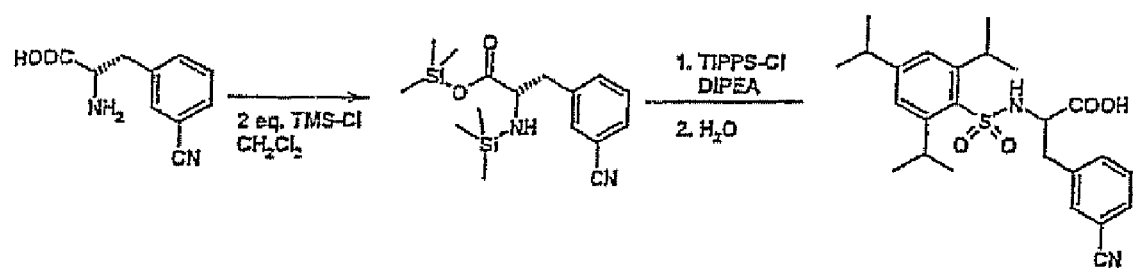

FIG. 4 shows a further embodiment of the method of the invention according to measure (e). The free amino acid L-3-CN-Phe is suspended together with an excess of trimethylsilane in dichloromethane and refluxed with stirring for 1.5 hours. By this means there is intermediate formation of the extremely water-sensitive trimethylsilyl ester as protection from dimerization. The simultaneous silylation of the amino group increases the nucleophilicity, thus speeding up the following reaction with TIPPS-Cl. Subsequently, the reaction solution is cooled in an ice bath, and DIPEA is added as base. TIPPS-Cl can be added all at once without special precautions (e.g. no dissolving or dropwise addition is necessary). The reaction solution is stirred at 0° C. for 30 minutes and then at room temperature for 1 to 2 hours. The solvent can subsequently be stripped off in vacuo. The residue is stirred in water for 5 minutes in order to eliminate the silyl ester and is then partitioned between 10 ml of ethyl acetate+30 ml of ether and 5% $KHSO_4$. The organic phase is washed twice with acid and twice with distilled water and dried, and the solvent is stripped off in vacuo. Evaporation was then carried out once with a little toluene, and the oil was dried in vacuo. The oil was mixed with 20 ml of petroleum ether and briefly treated in an ultrasonic bath, during which the product crystallizes out. The product was filtered off, washed with petroleum ether and then dried in vacuo. The yield was 849 of white crystalline powder. The purity measured by HPLC at 220 nm was 80%.

The invention claimed is:

1. A method for the production of 3-amidino- or 3-guanidinophenylalanine derivatives, comprising:
   a. reacting a 3-cyanophenylalanine with a quaternary ammonium hydroxide compound to form a 3-cyanophenylalanine ammonium salt;
   b. reacting the 3-cyanophenylalanine ammonium salt with an optionally substituted phenylsulfonyl halide.

2. The method of claim 1 wherein the optionally substituted phenylsulfonyl halide is a TIPPS halide;

3. The method of claim 2, wherein the TIPPS halide is a TIPPS-Cl.

4. The method of claim 1, wherein N-(2,4,6-triisopropylphenylsulfonyl)-3-amidino-(D,L)-phenyl-alanine 4-ethoxycarbonylpiperazide, N-(2,4,6-triisopropylphenylsulfonyl)-3-guanidino-(D,L)-phenylalanine 4-ethoxycarbonylpiperazide or the L enantiomers thereof are prepared.

* * * * *